(12) United States Patent
Sandhu et al.

(10) Patent No.: US 9,393,709 B2
(45) Date of Patent: Jul. 19, 2016

(54) MESH CAGE SCORING AND CUTTING SYSTEM

(71) Applicant: K2M, Inc., Leesburg, VA (US)

(72) Inventors: Faheem Sandhu, Washington, DC (US); Larry McClintock, Gore, VA (US); Kevin R. Strauss, Columbia, MD (US)

(73) Assignee: K2M, Inc., Leesburg, VA (US)

( * ) Notice: Subject to any disclaimer, the term of this patent is extended or adjusted under 35 U.S.C. 154(b) by 235 days.

(21) Appl. No.: 13/923,649

(22) Filed: Jun. 21, 2013

(65) Prior Publication Data

US 2013/0340590 A1 Dec. 26, 2013

Related U.S. Application Data

(60) Provisional application No. 61/664,209, filed on Jun. 26, 2012, provisional application No. 61/680,348, filed on Aug. 7, 2012.

(51) Int. Cl.

| B26D 3/08 | (2006.01) |
|---|---|
| A61B 17/88 | (2006.01) |
| B23D 21/08 | (2006.01) |
| B26D 3/16 | (2006.01) |
| B23D 21/14 | (2006.01) |
| B26B 25/00 | (2006.01) |

(52) U.S. Cl.
CPC .............. *B26D 3/08* (2013.01); *A61B 17/8863* (2013.01); *B23D 21/08* (2013.01); *B23D 21/145* (2013.01); *B26D 3/16* (2013.01); *B26D 3/169* (2013.01); *B26B 25/005* (2013.01); *Y10T 83/0341* (2015.04)

(58) Field of Classification Search
CPC ............ B26D 3/08; B26D 3/169; B26D 3/16; B23D 21/145; B23D 21/08; A61B 17/8863; B26B 25/005
USPC .......................... 83/13, 198; 30/102, 103, 108
See application file for complete search history.

(56) References Cited

U.S. PATENT DOCUMENTS

| 454,233 | A | * | 6/1891 | Smith | .............................. | 30/103 |
|---|---|---|---|---|---|---|
| 467,500 | A | * | 1/1892 | Fenwick | ......................... | 30/103 |
| 476,626 | A | * | 6/1892 | Fowler | .............................. | 30/103 |
| 482,496 | A | * | 9/1892 | Coppage | .......................... | 30/103 |
| 483,778 | A | * | 10/1892 | Chesterton | ....................... | 30/108 |
| 505,211 | A | * | 9/1893 | Adams | ............................. | 30/103 |
| 513,965 | A | * | 1/1894 | Fenwick | ......................... | 30/103 |
| 729,109 | A | * | 5/1903 | Warner | .............................. | 30/108 |
| 828,120 | A | * | 8/1906 | Jones | ............................... | 30/103 |

(Continued)

OTHER PUBLICATIONS

European Search Report dated Oct. 2, 2013 for EP 13 17 3785.

*Primary Examiner* — Sean Michalski
(74) *Attorney, Agent, or Firm* — Carter, DeLuca, Farrell & Schmidt, LLP

(57) ABSTRACT

A scoring system includes a scoring device and a mandrel. The scoring device includes at least one scoring disc configured to engage a surface of a mesh cage. In an open condition, the scoring disc is positioned away from the mesh cage and in a closed condition, the scoring disc engages a surface of the mesh cage. The scoring device is rotatable about the longitudinal axis of the mesh cage when in the closed condition to score the mesh cage at a desired length from an end of the mesh cage. The mandrel is insertable within the mesh cage to support and/or retain a portion of the mesh cage. The mandrel can also apply a force to the score mark to cleanly separate two portions of the mesh cage at the score mark.

7 Claims, 8 Drawing Sheets

(56) References Cited

U.S. PATENT DOCUMENTS

| | | | | |
|---|---|---|---|---|
| 936,674 | A * | 10/1909 | Skinner | 30/108 |
| 1,028,870 | A * | 6/1912 | Fletcher | 30/103 |
| 1,435,467 | A | 11/1922 | Harman | |
| 1,674,440 | A | 6/1928 | McCloskey | |
| 1,945,949 | A | 2/1934 | Myers | |
| 2,016,735 | A | 10/1935 | Abramson et al. | |
| 2,271,033 | A | 1/1942 | Petersen | |
| 2,283,572 | A | 5/1942 | Peterson | |
| 2,325,353 | A | 7/1943 | Wright | |
| 2,345,166 | A * | 3/1944 | Williams, Jr. | C03B 33/04 266/64 |
| 2,350,667 | A | 6/1944 | Bates | |
| 2,360,887 | A | 10/1944 | Parker | |
| 2,379,177 | A | 10/1945 | Pavey | |
| 2,491,543 | A * | 12/1949 | Alfonso | 74/424.78 |
| 2,502,700 | A * | 4/1950 | Capewell | 30/102 |
| D158,536 | S | 5/1950 | Wolcott | |
| 2,511,358 | A | 6/1950 | Mayer et al. | |
| 2,526,471 | A | 10/1950 | Ginns | |
| 2,556,974 | A | 6/1951 | Nye, Jr. | |
| 2,557,737 | A | 6/1951 | Franck | |
| 2,563,483 | A * | 8/1951 | Alfonso | 30/102 |
| 2,582,406 | A * | 1/1952 | Herman Bachli et al. | 30/102 |
| 2,622,323 | A * | 12/1952 | Grimaldi | 30/101 |
| 2,629,926 | A | 3/1953 | Franck | |
| 2,630,028 | A | 3/1953 | McIntosh | |
| 2,630,029 | A | 3/1953 | Franck | |
| 2,659,253 | A * | 11/1953 | Myrick | 225/93 |
| 2,666,984 | A | 1/1954 | Shafer | |
| 2,706,853 | A | 4/1955 | Wilson | |
| 2,716,280 | A | 8/1955 | Ruhe | |
| 2,718,058 | A | 9/1955 | Arnold | |
| 2,747,275 | A | 5/1956 | Jonasson | |
| 2,787,054 | A | 4/1957 | Franck | |
| 2,796,663 | A | 6/1957 | Karnes | |
| 2,814,867 | A | 12/1957 | Charles | |
| 2,817,898 | A | 12/1957 | Vermette | |
| 2,870,535 | A | 1/1959 | Vermette | |
| 2,871,733 | A | 2/1959 | Lauck | |
| 2,875,518 | A | 3/1959 | Dyczynski | |
| 2,877,549 | A | 3/1959 | Landreth | |
| 2,915,819 | A * | 12/1959 | O'Day et al. | 30/103 |
| 2,921,369 | A * | 1/1960 | Stanley | 30/102 |
| 2,993,274 | A | 7/1961 | Dirks | |
| 3,008,231 | A | 11/1961 | Caproni | |
| 3,013,335 | A | 12/1961 | Kowal | |
| 3,022,575 | A | 2/1962 | Wright | |
| 3,031,237 | A | 4/1962 | Weibel | |
| 3,070,885 | A | 1/1963 | Musy et al. | |
| 3,082,523 | A | 3/1963 | Modes et al. | |
| 3,097,428 | A | 7/1963 | Lutsker | |
| 3,100,934 | A | 8/1963 | Jonasson | |
| 3,106,776 | A | 10/1963 | Plas | |
| 3,117,375 | A | 1/1964 | Meese | |
| 3,118,227 | A | 1/1964 | Samuels et al. | |
| 3,157,328 | A * | 11/1964 | Werner Hennings et al. | 225/2 |
| 3,171,199 | A | 3/1965 | Meese | |
| 3,196,652 | A | 7/1965 | Meese | |
| 3,237,301 | A * | 3/1966 | Wilson | 30/102 |
| 3,240,088 | A | 3/1966 | Samuels et al. | |
| 3,335,492 | A * | 8/1967 | Spiro | 30/101 |
| 3,376,638 | A | 4/1968 | Bjalme et al. | |
| 3,403,442 | A | 10/1968 | Reese et al. | |
| 3,408,738 | A | 11/1968 | Schade | |
| 3,520,057 | A | 7/1970 | Gore et al. | |
| 3,545,081 | A | 12/1970 | Butler | |
| 3,608,194 | A | 9/1971 | Miller | |
| 3,624,682 | A | 11/1971 | Kowal | |
| 3,651,569 | A | 3/1972 | Arnot | |
| 3,885,261 | A | 5/1975 | Skvarenina | |
| 3,932,937 | A | 1/1976 | Bastiansen | |
| 4,078,304 | A * | 3/1978 | Netzel | 30/101 |
| 4,103,419 | A | 8/1978 | Matthews et al. | |
| 4,114,485 | A | 9/1978 | Coblitz et al. | |
| 4,132,100 | A | 1/1979 | Schuler | |
| 4,174,646 | A | 11/1979 | Kotler | |
| 4,177,557 | A | 12/1979 | Courty | |
| 4,305,205 | A | 12/1981 | Girala | |
| 4,345,376 | A * | 8/1982 | Benson et al. | 30/96 |
| 4,438,562 | A * | 3/1984 | Courty | 30/99 |
| 4,577,406 | A * | 3/1986 | Idzik et al. | 30/103 |
| 4,858,316 | A | 8/1989 | Dubey | |
| 5,099,577 | A * | 3/1992 | Hutt | 30/101 |
| 5,203,083 | A | 4/1993 | Domonoske | |
| 5,206,996 | A | 5/1993 | McDaniel | |
| 5,230,150 | A | 7/1993 | Sperti | |
| 5,345,682 | A | 9/1994 | Dubinsky et al. | |
| 5,414,932 | A * | 5/1995 | Azkona | 30/96 |
| 5,515,609 | A | 5/1996 | Sperti | |
| 5,581,886 | A * | 12/1996 | Sesser et al. | 30/101 |
| 5,592,741 | A * | 1/1997 | Vassar | B23D 21/08 30/101 |
| 5,903,980 | A | 5/1999 | Collier et al. | |
| 5,943,778 | A * | 8/1999 | Alana | 30/101 |
| 5,988,027 | A | 11/1999 | Lenox | |
| 6,055,732 | A | 5/2000 | Hu | |
| 6,073,526 | A * | 6/2000 | Pettersson | 83/54 |
| 6,134,997 | A | 10/2000 | Rosanova | |
| 6,202,307 | B1 | 3/2001 | Wrate | |
| 6,226,823 | B1 | 5/2001 | Ma Gee | |
| 6,237,449 | B1 | 5/2001 | Orlosky | |
| 6,393,700 | B1 | 5/2002 | Babb | |
| 6,401,340 | B1 | 6/2002 | King | |
| 6,609,302 | B2 | 8/2003 | Welker et al. | |
| 6,658,739 | B1 * | 12/2003 | Huang | 30/96 |
| 6,739,055 | B2 | 5/2004 | Lee | |
| 6,776,798 | B2 * | 8/2004 | Camino et al. | 623/17.16 |
| 7,275,320 | B2 | 10/2007 | Lee | |
| 7,316,069 | B2 * | 1/2008 | Graybeal | 30/92 |
| RE40,461 | E | 8/2008 | Hu | |
| 7,513,180 | B2 * | 4/2009 | Minowa et al. | 82/101 |
| 7,591,072 | B2 | 9/2009 | Stravitz | |
| 7,624,663 | B2 * | 12/2009 | Kaehr et al. | 83/456 |
| 7,934,317 | B2 | 5/2011 | Chiu | |
| 2002/0121173 | A1 * | 9/2002 | Filipo | 83/880 |
| 2005/0125986 | A1 * | 6/2005 | Pham et al. | 29/557 |
| 2005/0274022 | A1 | 12/2005 | Korczak et al. | |
| 2006/0059692 | A1 * | 3/2006 | Lee | 30/101 |
| 2007/0209495 | A1 | 9/2007 | Marcon | |
| 2007/0251095 | A1 | 11/2007 | Nagasoe | |
| 2008/0000091 | A1 | 1/2008 | Eriguchi | |
| 2008/0011133 | A1 * | 1/2008 | Karahalios et al. | 83/13 |
| 2008/0060203 | A1 | 3/2008 | Metcalf | |
| 2009/0049697 | A1 | 2/2009 | Williams | |
| 2009/0090008 | A1 | 4/2009 | Nagasoe | |
| 2009/0293288 | A1 * | 12/2009 | Hernandez | 30/251 |
| 2010/0088898 | A1 * | 4/2010 | Thorson et al. | 30/95 |
| 2010/0199499 | A1 * | 8/2010 | Dibble | 30/102 |
| 2010/0205809 | A1 | 8/2010 | Lier et al. | |
| 2010/0305682 | A1 * | 12/2010 | Furst | 623/1.13 |
| 2011/0084108 | A1 * | 4/2011 | McClintock et al. | 225/2 |
| 2012/0041540 | A1 * | 2/2012 | Shobayashi et al. | 623/1.15 |
| 2013/0096669 | A1 * | 4/2013 | Bregulla et al. | 623/1.16 |
| 2014/0366382 | A1 * | 12/2014 | Krause et al. | 30/97 |

\* cited by examiner

MESH CAGE SCORING AND CUTTING SYSTEM

CROSS-REFERENCE TO OTHER APPLICATIONS

This application claims priority to and the benefit of U.S. Provisional Application Ser. No. 61/664,209 filed Jun. 26, 2012, and U.S. Provisional Application Ser. No. 61/680,348 filed Aug. 7, 2012, the disclosure of each is hereby incorporated by reference in its entirety.

BACKGROUND

1. Technical Field

The present disclosure relates to surgical devices for use in spinal surgery and, more specifically, to surgical mesh cages used in spinal surgery.

2. Discussion of Related Art

Disease, the effects of aging, or physical trauma resulting in damage to the spine has been treated in many instances by fixation or stabilization of the effected vertebra. A wide variety of spinal fixation apparatuses have been employed in surgical procedures for correction of spinal injuries and the effects of spinal diseases. Many of these apparatuses commonly use a pair of longitudinal rods running in a relatively parallel relationship to each other in combination with a mesh cage that is inserted between the vertebral bodies of the spinal column, such mesh cages are commonly constructed of titanium.

Mesh cages must be provided in a desired mesh cage length for each patient. To provide mesh cages of a desired length, medical facilities may stock only one mesh cage length to allow for a reduced inventory and to give the surgeon the ability to cut the mesh cage to the exact size needed. One method of cutting a mesh cage is for the surgeon to use a pair of tin snips to cut the mesh cage to the desired length. This method is time-consuming and leaves jagged edges to the device which can cause damage to the anatomy of the patient. Alternatively, to provide mesh cages of a desired length, medical facilities can have a large inventory of mesh cages in varying sizes and configurations. However, this is not economical nor is it the best solution for the patient as the patient may need a size between ones that are available in inventory.

Therefore, a need exists for a device that can efficiently and cleanly cut a mesh cage to a desired length while not damaging the cage and provide a smooth edge to the cut mesh cage so it does not cause damage to the surrounding tissue and vasculature of the patient.

SUMMARY

In an aspect of the present disclosure, a surgical system for providing a mesh cage includes a mesh cage and a scoring device. The scoring device includes a fixed body having proximal and distal ends, a handle, a threaded rod coupled to the handle, first and second arms, and at least one scoring disc. The first and second arms are positioned at the distal end of the fixed body and are movable with respect to one another between an open and closed condition. The at least one scoring disc is rotatably coupled to one of the first or second arms. The at least one scoring disc is configured to engage the mesh cage when the first and second arms are in the closed condition. The system can also include a mandrel having a cage support. The cage support is positionable within an inner channel of the mesh cage. The mandrel can include a handle and a bent portion. The bent portion defines an angle between the handle and the cage support. The mandrel can further include a retention assembly. The retention assembly is configured to secure the mesh cage to the mandrel in a fixed position.

In embodiments, the first arm of the scoring device is fixed to the distal end of the fixed body and is C-shaped and the second arm is slidably positioned within an opening in the distal end of the fixed body. The second arm has a first position and a second position corresponding to the open and closed conditions respectively. The second arm is operatively associated with the threaded rod such that the threaded rod moves the second arm between the first and second positions.

In some embodiments, the first and second arms of the scoring device each have a proximal end pivotally coupled to the fixed body. The threaded rod engages the proximal ends of each of the first and second arms to move the first and second arms between the open and closed conditions. The at least one scoring disc can be rotatably coupled to the distal end of the first arm and a rotatable anvil can be rotatably coupled to the distal end of the second arm.

According to another aspect of the present disclosure, a method for cutting a mesh cage includes providing a mesh cage, creating a score mark, and removing a portion of the mesh cage. Providing a mesh cage includes providing a mesh cage having first and second ends and having a first length. Creating a score mark includes creating a score mark on the mesh cage at a position corresponding to a second length from an end of the mesh cage with a scoring device, the second length different from the first length. Removing a portion of the mesh cage includes removing a portion of the mesh cage beyond the score mark.

Creating a score mark may include cutting through the mesh cage with the scoring device. Creating the score mark may include rotating and/or oscillating the scoring device about a longitudinal axis of the mesh cage.

The method may further include inserting a mandrel through an end of the mesh cage before creating the score mark. The method may also include retaining the mesh cage in a fixed position to the cage support of the mandrel with a retaining mechanism.

In embodiments, the method includes inserting an end of a mandrel through the first end of the mesh cage and inserting an end of a second mandrel through the second end of the mesh cage after scoring the mesh cage, the end of the first mandrel positioned near the score mark between the score mark and the first end of the mesh cage and the end of the second mandrel positioned near the score mark between the score mark and the second end of the mesh cage. The method may further include applying a force to another end of each of the mandrel and the second mandrel to remove the portion of the mesh cage beyond the score mark.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
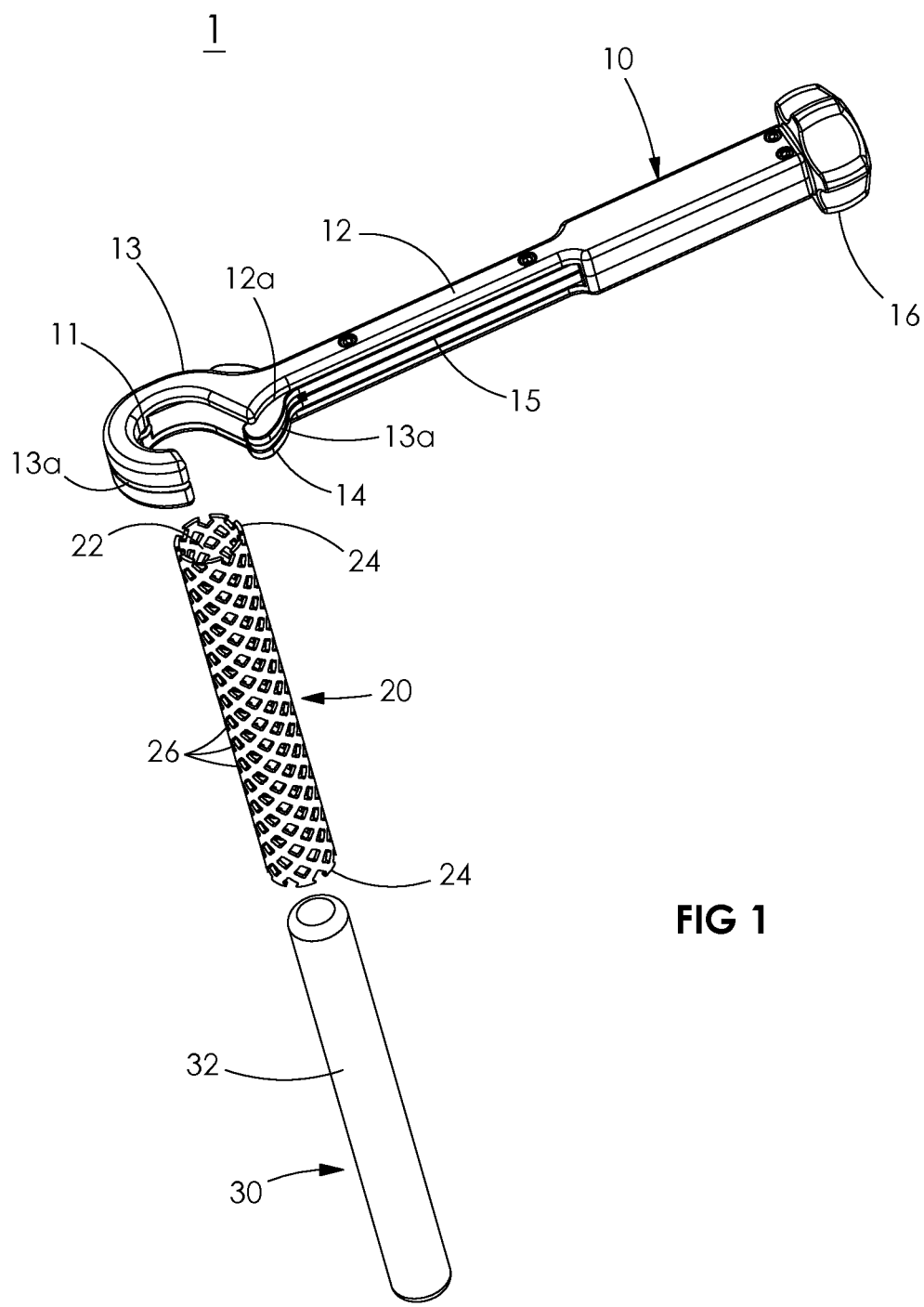
FIG. 1 is a perspective view of the components of a system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, a surgeon, or any other care provider and may include support personnel. Throughout this description, the term "proximal" will refer to the portion of the device or component thereof that is closest to the clinician and the term "distal" will refer to the portion of the device or component thereof that is furthest from the clinician.

Referring now to FIG. 1, a system 1 for providing a mesh cage of a desired length is provided in accordance with the present disclosure including a scoring device 10, a mesh cage 20, and a mandrel 30.

Scoring device 10 includes at least one scoring blade or disc 11, a fixed body 12, a first arm or jaw 13, a second arm or jaw 14, and a rotatable knob 16. First jaw 13 is generally C-shaped and is fixed to the distal end of fixed body 12 and second jaw 14 is slidably received within an opening 12a in the distal end of fixed body 12. Second jaw 14 is operatively associated with and positioned at the distal end of a threaded rod 15. The proximal end of threaded rod 15 is coupled to handle or rotatable knob 16 and configured to cooperate with the rotation of rotatable knob 16. Scoring disc 11 is positioned within first jaw 13 and defines a cutting plane about its center. In embodiments, scoring disc 11 is removably positioned within first jaw 13. In such embodiments, scoring disc 11 may be removed and replaced. In some embodiments, first jaw 13 includes more than one scoring disc 11 spaced about the inner surface of first jaw 13 and/or second jaw 14 with each scoring disc 11 located on a common cutting plane. In certain embodiments, first jaw 13 and/or second jaw 14 include indicia of the location of the cutting plane. In particular embodiments, the indicium of the location of the cutting plane is a groove 13a in the outer surface of first jaw 13 and/or second jaw 14.

Figure 2:
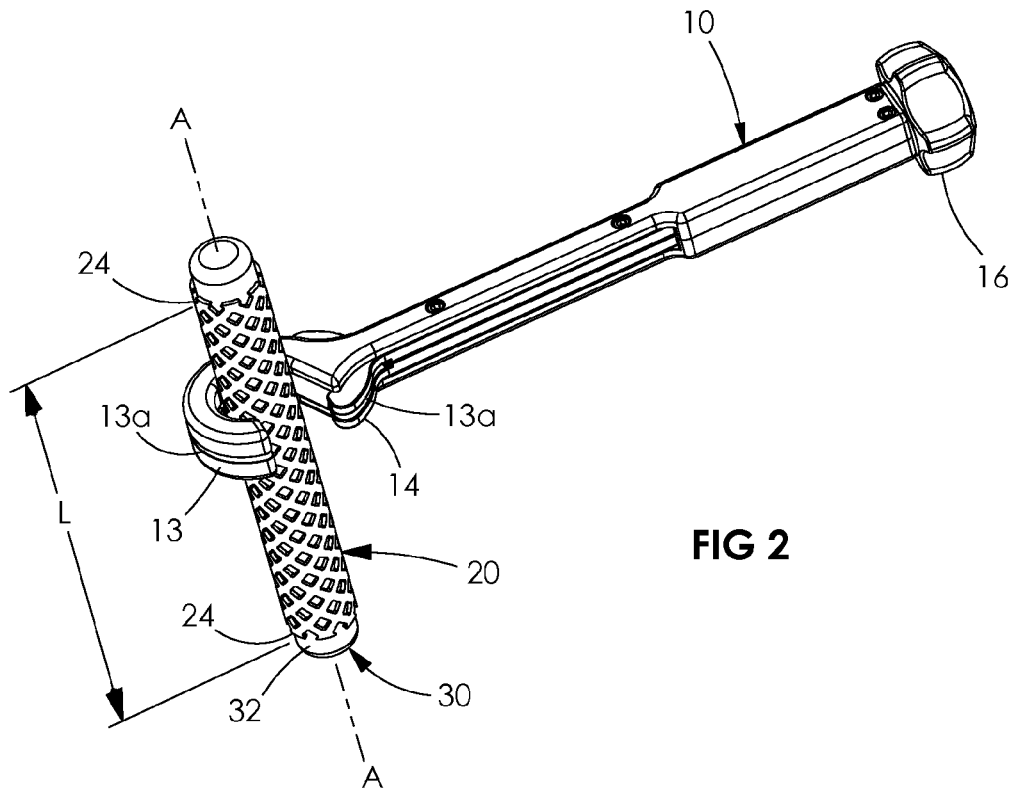
FIG. 2 is a perspective view of the components of the system of FIG. 1 with the mesh cage positioned on the mandrel and the jaws of the scoring device in the open position.
Figure 3:
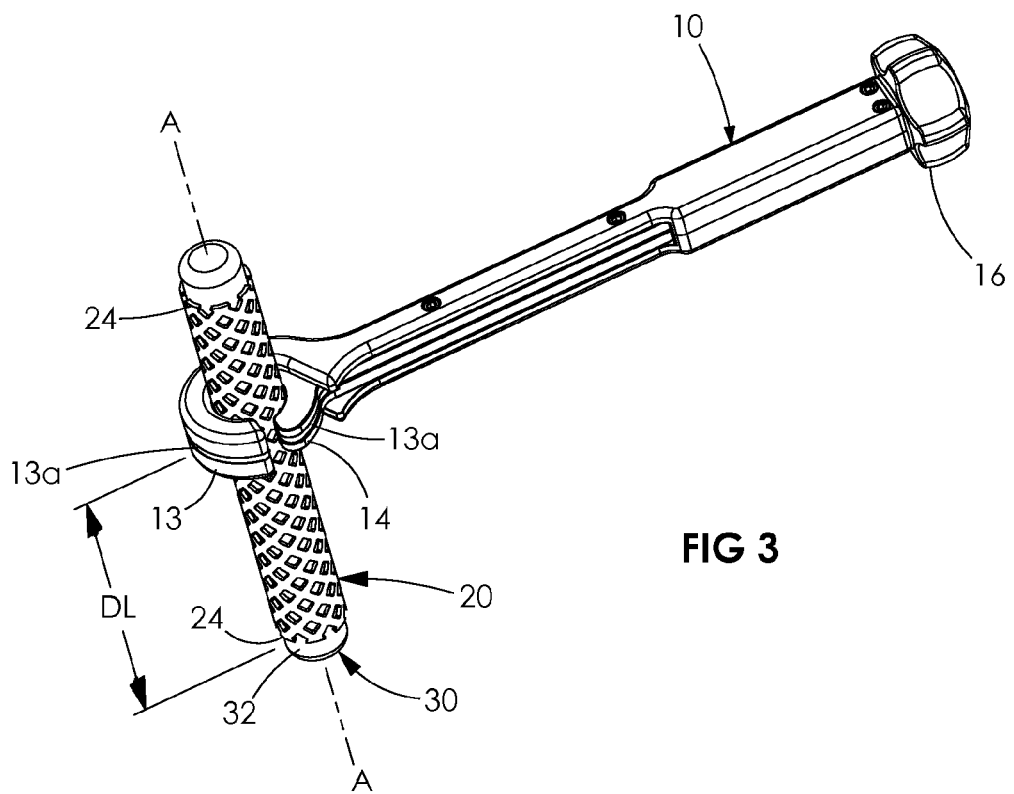
FIG. 3 is a perspective view of the components of the system of FIG. 1 with the jaws of the scoring device in the closed condition.

Referring to FIGS. 2 and 3, first and second jaws 13, 14 are movable with respect to each other having an open condition and a closed condition. Rotation of rotatable knob 16 moves second jaw 14 between a first position (FIG. 2) and a second position (FIG. 3) corresponding to the open condition and the closed condition of jaws 13 and 14, respectively. The size of the opening in the closed condition is approximately equal to the outer diameter of the mesh cage.

Referring back to FIGS. 1 and 2, mesh cage 20 is generally tubular in shape including an inner channel 22 between open ends 24. A length "L" is defined between ends 24 along a longitudinal axis "A-A". The outer surface of mesh cage 20 includes a plurality of openings 26. Each end 24 of mesh cage 20 is generally planar and can be offset at an angle with respect to an axis perpendicular to longitudinal axis "A-A". The angle of offset can be in a range of about 0° to about 45° and correspond to the lordosis of the patient. Mesh cage 20 can be provided with varying inner and outer diameters.

Mandrel 30 includes a cage support 32 sized and configured to be received within the inner channel 22 of mesh cage 20 and has a length at least equal to length "L" of mesh cage 20. Cage support 32 of mandrel 30 is configured to provide support for mesh cage 20 to prevent mesh cage 20 from deflecting inward when a force is applied to the outer surface of mesh cage 20, e.g., cage support 32 prevents the crushing or damaging of mesh cage 20 during the scoring process described below.

Referring now to FIGS. 2-5, scoring device 10 is used in accordance with the present disclosure to provide a mesh cage having a desired length. Mesh cage 20 is provided having an inner and outer diameter for a given patient and having a length "L" greater than a desired length "DL". Mandrel 30 is positioned within inner channel 22 of mesh cage 20 such that cage support 32 of mandrel 30 supports the inner surface of mesh cage 20 as shown in FIG. 2.

With continued reference to FIG. 2, jaws 13, 14 of scoring device 10 are in the open condition such that mesh cage 20 is positionable between first and second jaws 13, 14. Scoring disc 11 of scoring device 10 is positioned such that the cutting plane of scoring disc 11 corresponds to desired length "DL" of the mesh cage from an end 24 of mesh cage 20. Rotatable handle 16 is rotated to move second jaw 14 from the first position to the second position such that the outer surface of mesh cage 20 is grasped between first and second jaws 13, 14 as shown in FIG. 3. When the first and second jaws 13, 14 grasp the outer surface of mesh cage 20, jaws 13, 14 of scoring device 10 are in the closed condition and scoring disc 11 engages the outer surface of mesh cage 20.

Figure 4:
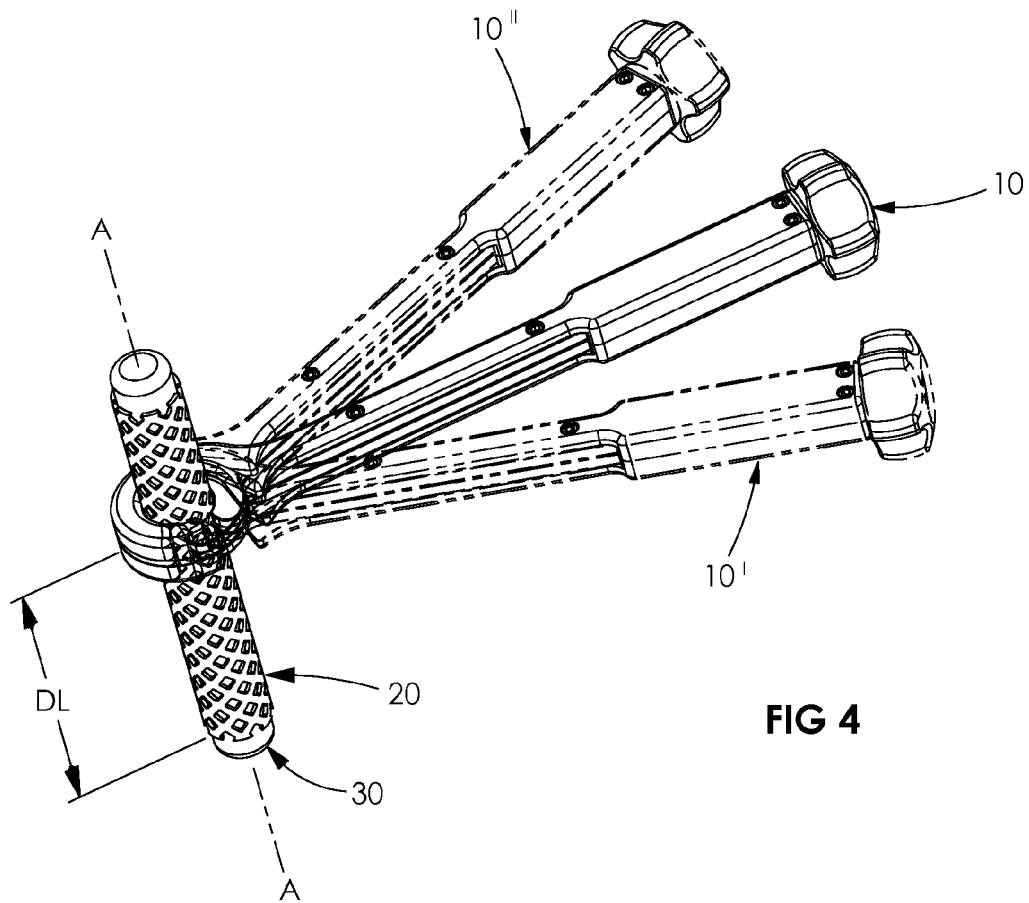
FIG. 4 is a perspective view of the components of the system of FIG. 1 with the jaws of the scoring device in the closed condition and the cutting plane of the scoring disc positioned at the desired length illustrating oscillation of the scoring device about the mesh cage.
Figure 5:
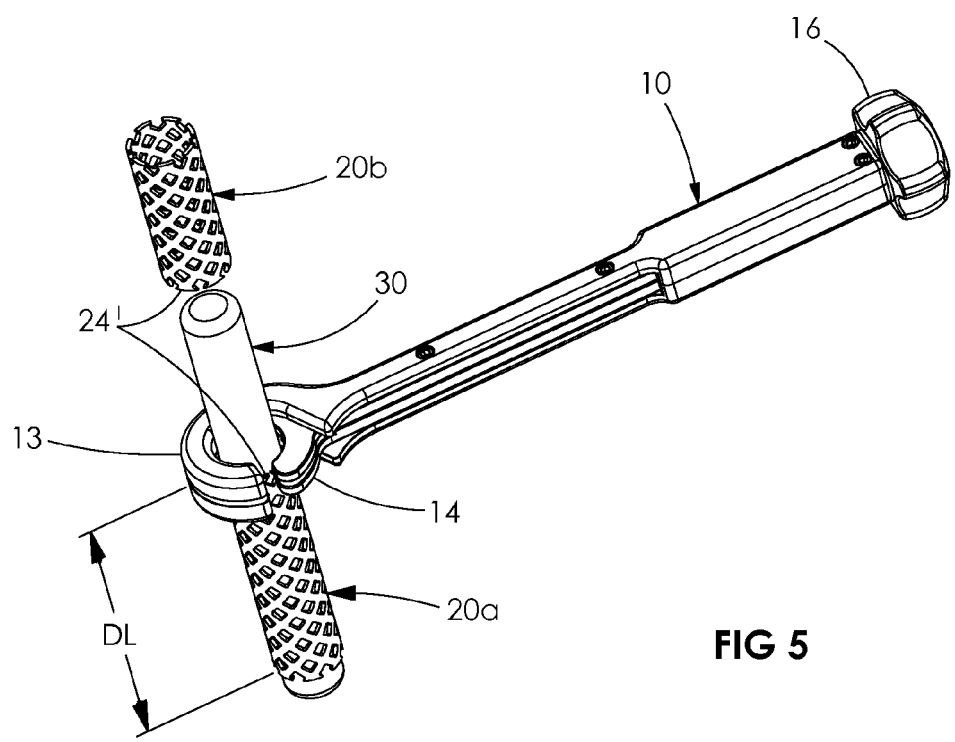
FIG. 5 is a perspective view of the components of the system of FIG. 1 with a portion of the mesh cage separated from another portion of the mesh cage.

Referring to FIG. 4, scoring device 10 is rotated or oscillated about the longitudinal axis "A-A" in a clockwise and/or counter clockwise direction as illustrated by scoring devices 10' and 10". As scoring device 10 is rotated, scoring disc 11 scores the outer surface of mesh cage 20 about the cutting plane that corresponds to the desired length "DL" from an end 24 of mesh cage 20. As shown in FIG. 5, scoring disc 11 can cut through mesh cage 20 about the cutting plane separating a first portion 20a of mesh cage 20 from a second portion 20b of mesh cage 20. At least one of first and second portions 20a, 20b has a length corresponding to the desired length "DL". Scoring disc 11 cuts mesh cage 20 smoothly about the cutting plane such that ends 24' of the cut do not harm the patient.

Figure 6A:
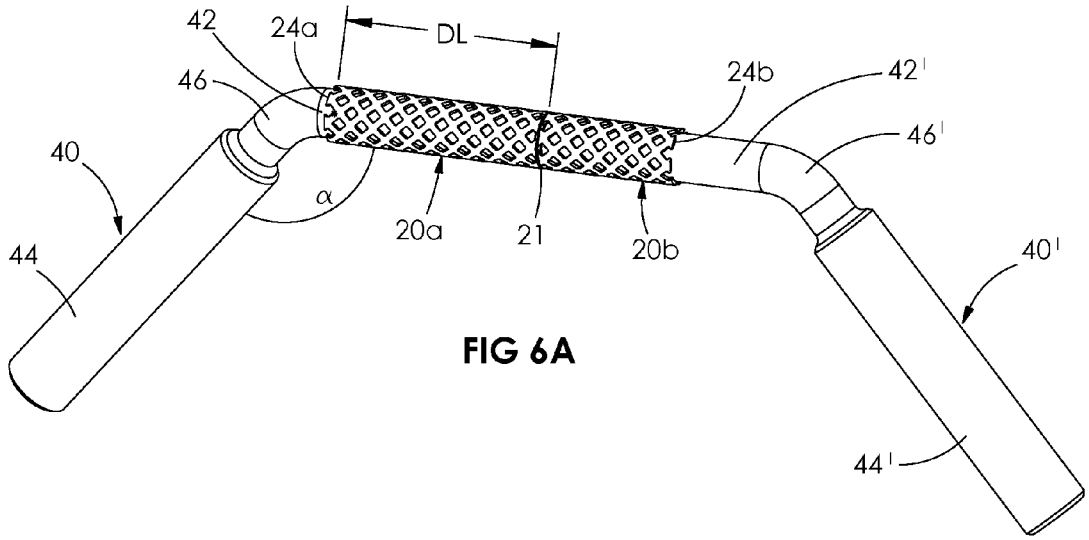
FIGS. 6A-C are a progression of perspective views of another mandrel in accordance with the present disclosure being used to separate two portions of a mesh cage at a score mark.
Figure 6B:
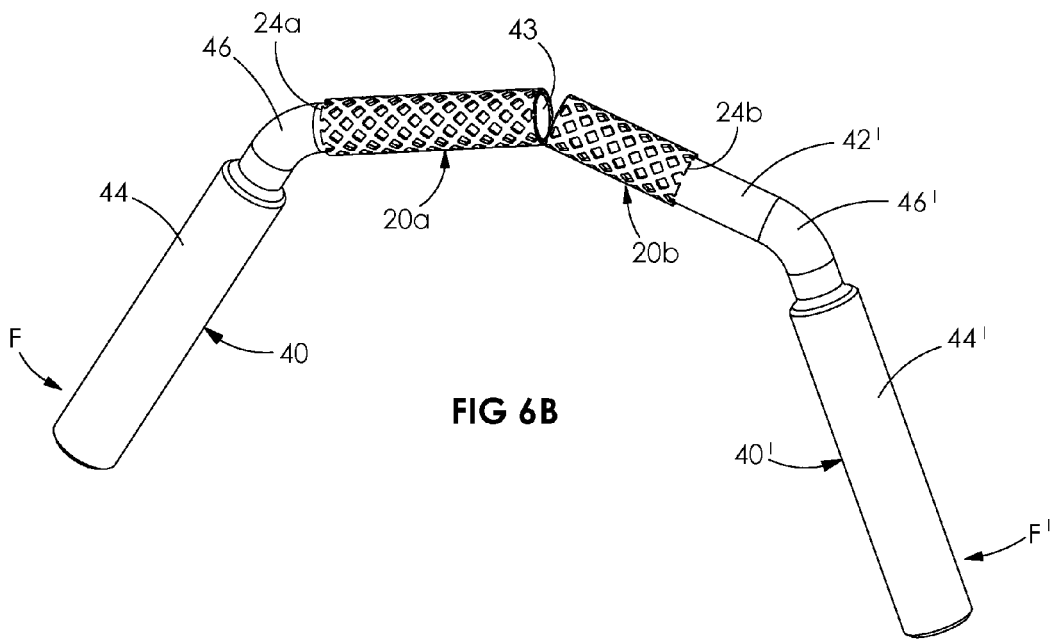
Figure 6C:
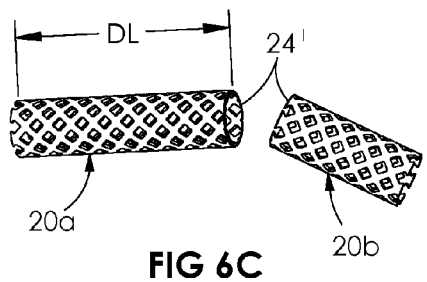

Referring to FIGS. 6A-6C, when scoring disc 11 scores the outer surface of mesh cage 20 without cutting entirely through mesh cage 20, another mandrel 40 can be used in accordance with the present disclosure to provide additional energy to the scored area of mesh cage 20 to separate mesh cage 20 into two portions 20a, 20b with smooth ends 24' at score mark 21. Mandrel 40 includes a cage support 42 which is substantially similar to cage support 32 of mandrel 30 discussed above, as such only the differences of mandrel 40 will be discussed in detail below. If necessary or desired, the jaws may be tightened around the mesh after the mesh has partially been scored, and rotation or oscillation continued thereafter to further score the mesh cage.

In embodiments, mandrel 40 includes a handle 44. In some embodiments, mandrel 40 includes a bent portion 46 between cage support 42 and handle 44 that define an angle α between cage support 42 and handle 44.

After mesh cage 20 is scored, a mandrel 40 is inserted through end 24a of mesh cage 20 such that an end 43 (FIG. 6B) is positioned near but not past score mark 21 and a second mandrel 40' is inserted through end 24b such that an end (not shown) is positioned near but not past score mark 21. End 43 of mandrel 40 and the end of mandrel 40' are spaced-apart defining a gap between the ends when mandrels 40 and 40' are positioned within mesh cage 20. When mandrels 40 and 40' are positioned within mesh cage 20, a force F, F' is applied to each handle 44, 44' which is transferred by mandrels 40, 40' to mesh cage 20 near score mark 21. The energy of force F, F' separates mesh cage 20 at score mark 21 into two portions 20a, 20b.

Additionally, mandrel 40 can support mesh cage 20 while scoring device 10 creates score mark 21. Mandrel 40 is inserted within inner channel 22 of mesh cage 20 through an end 24a of mesh cage 20 such that an end 43 (FIG. 6B) of mandrel 40 is between the location of the cut or score mark 21 and end 24b of mesh cage 20. It can be appreciated that the location of score mark 21 corresponds to the desired length "DL". Scoring device 10 scores the outer surface of mesh cage 20 creating a score mark 21 as discussed above. An end 43 (FIG. 6B) of cage support 42 is positioned near score mark 21 between score mark 21 and end 24a of mesh cage 20. A force "F" is applied to handle 44 while end 24b of mesh cage 20 is held stationary to apply additional energy to score mark 21. The additional energy separates mesh cage 20 into two portions 20a, 20b. In embodiments, a cage support 42' of a second mandrel 40' is inserted into mesh cage 20 such that an end 43' of second mandrel 40' is near score mark 21 between score mark 21 and end 24b of mesh cage 20.

Figure 7A:
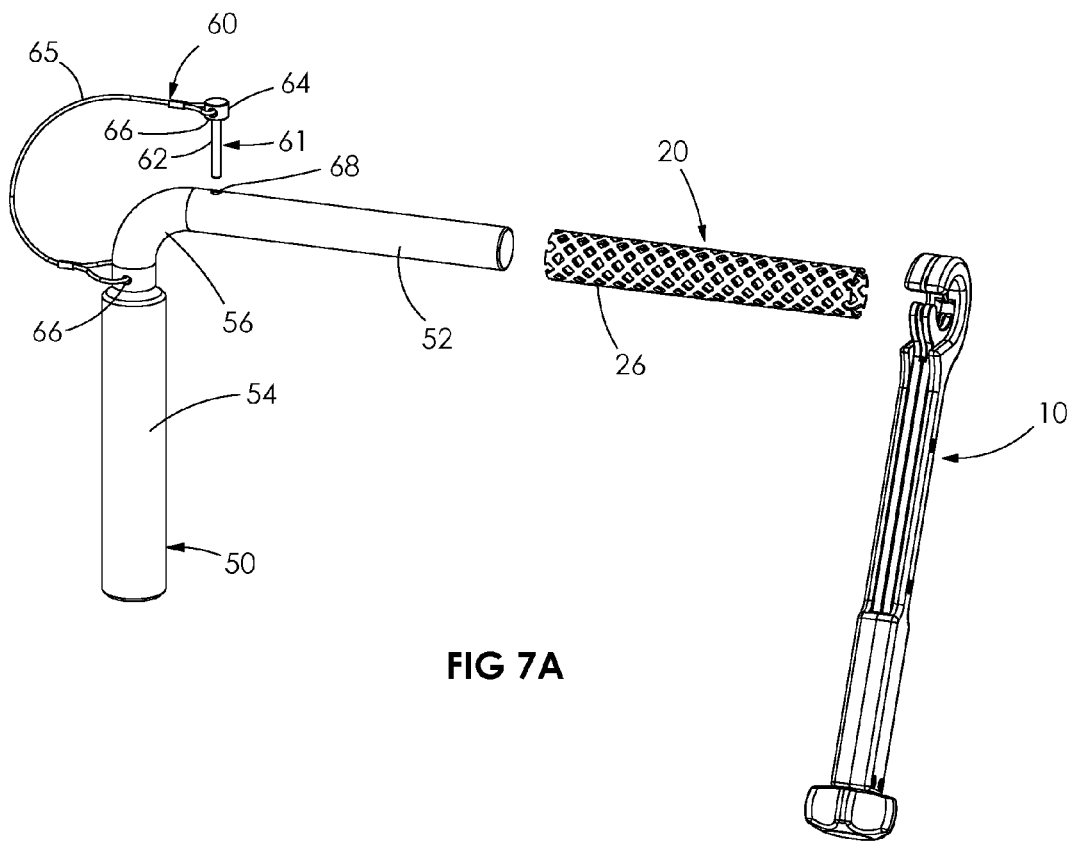
FIGS. 7A and 7B are perspective views of yet another mandrel in accordance with the present disclosure including a retaining mechanism.
Figure 7B:
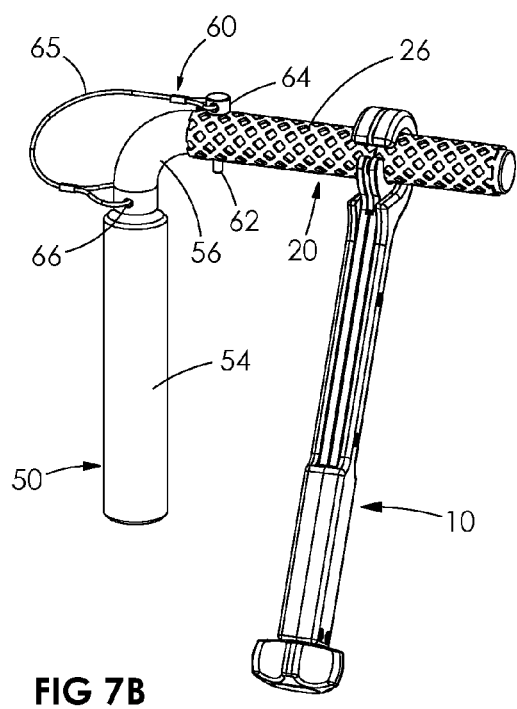

Referring to FIGS. 7A and 7B, a mandrel 50 is provided in accordance with the present disclosure incorporating a cage support 52, a handle 54, a bent portion 56, and a retainer mechanism 60. Cage support 52, handle 54, and bent portion 56 of mandrel 50 are substantially similar to cage support 42, handle 44, and bent portion 46 of mandrel 40 described above, and as such only the differences will be discussed in detail below.

Retainer mechanism 60 includes a pin 61 and a cord 65. Pin 61 includes a body 62 and a head 64 positioned at an end of body 62. Body 62 is sized and configured to pass through openings 26 of mesh cage 20 as shown in FIG. 7B. Cage support 52 includes a pin hole 68 sized and configured to receive body 62 of pin 61 while inhibiting head 64 of pin 61 from passing therethrough. Head 64 and handle 54 can each include a through hole 66 sized and configured to receive an end of a cord 65. An end of cord 65 passes through and is secured in through holes 66 to retain pin 61 to mandrel 50.

With additional reference to FIG. 7B, when mesh cage 20 is positioned around cage support 52, pin 61 is passed through openings 26 in mesh cage 20 and pinhole 68. Pin 61 prevents mesh cage 20 from rotating about cage support 52 while scoring device 10 scores and/or cuts mesh cage 20, i.e., maintains mesh cage 20 in a fixed position relative to mandrel 50, i.e. fixed radially and axially.

Figure 8:
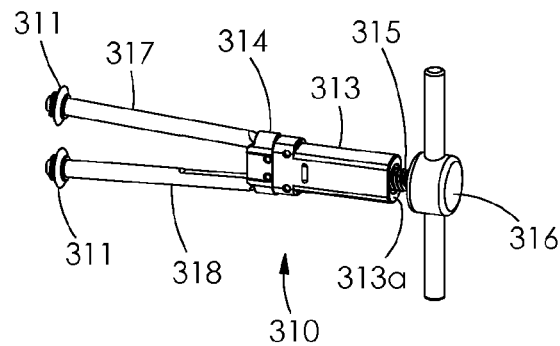
FIG. 8 is a perspective view of another scoring device in accordance with the present disclosure including inner and outer arms.

Referring to FIG. 8, a scoring device 310 is provided in accordance with the present disclosure incorporates scoring discs 311, a first or outer arm 317, a second or inner arm 318, and a fixed body 313. Outer arm 317 and inner arm 318 each have a scoring disc 311 rotatably coupled to a distal end thereof. The proximal end of each of outer arm 317 and inner arm 318 are pivotally coupled to a pivot joint 317 positioned at a distal end of fixed body 313. In embodiments, one of arms 317, 318 can be coupled to pivot joint 314 in a fixed position relative to fixed body 313. Fixed body 313 includes a threaded hole 313a extending from its proximal end to pivot joint 314. Threaded hole 313a can be threaded from the proximal end of fixed body 313 to pivot joint 314 or only a portion of threaded hole 313a can be threaded between the proximal end of fixed body 313 and pivot joint 314. A threaded rod 315 is inserted through threaded hole 313a such that the threads of threaded rod 315 cooperate with the threads of threaded hole 313a. A rotational knob or handle 316 is coupled to the proximal end of threaded rod 315.

Figure 9:
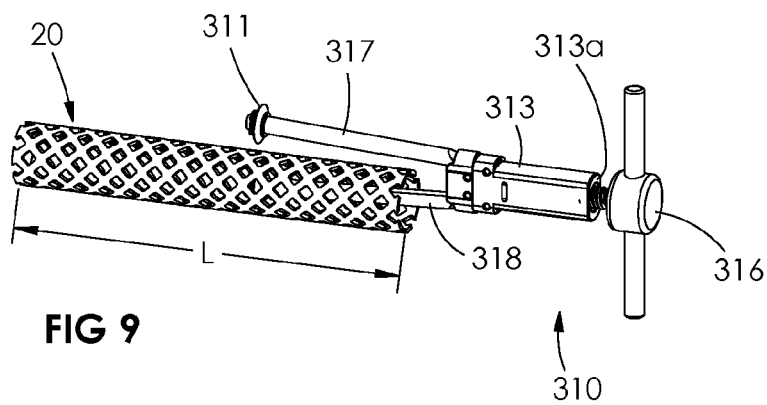
FIGS. 9-11 are a progression of the scoring device of FIG. 8 being used to score a mesh cage
Figure 10:
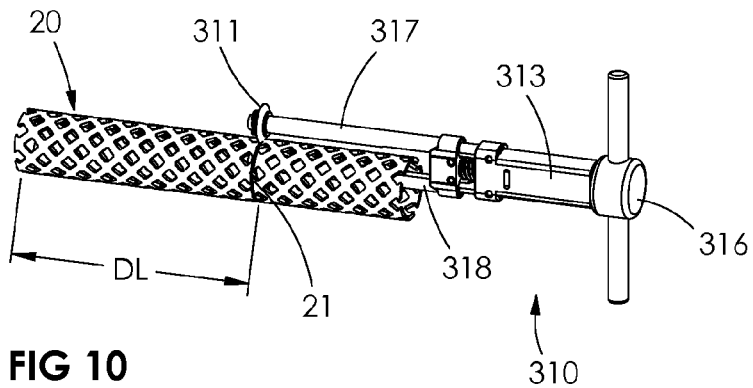

Referring to FIGS. 9 and 10, scoring device 310 has an open condition (FIG. 9) and a closed condition (FIG. 10). In the open condition, arms 317, 318 of scoring device 310 are spaced-apart defining a gap between scoring discs 311 and in the closed condition, arms 317, 318 of scoring device 310 are moved towards each other to reduce and/or close the gap between scoring discs 311. Threaded rod 315 is operatively associated with outer arm 317 and inner arm 318 to move the arms 317, 318 between the open and closed conditions.

Figure 11:
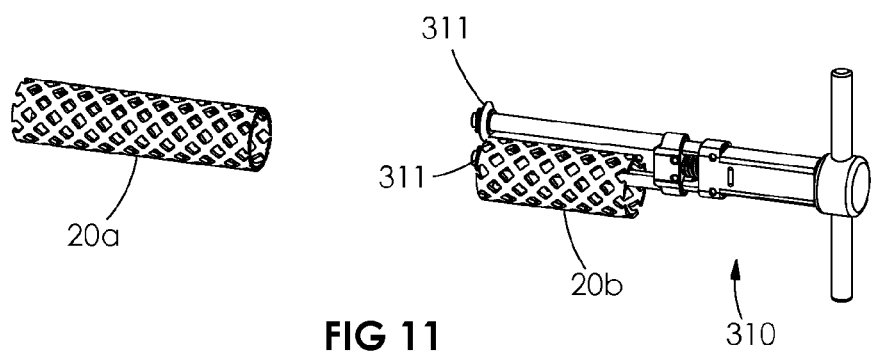

Referring to FIGS. 9-11, scoring device 310 is used in accordance with the present disclosure to provide a mesh cage having a desired length. As shown in FIG. 9, scoring device 310 is in the open condition such that a mesh cage 20 having a length "L" is positionable about inner arm 318. It will be appreciated that the gap between scoring discs 311 is greater than the thickness of mesh cage 20. Mesh cage 20 is positioned about inner arm 318 such that scoring discs 311 define a desired length "DL" from an end of the mesh cage 20 as shown in FIG. 10. In embodiments, scoring disc 311 rotatably coupled to the end of inner arm 318 is sized such that the longitudinal axis of inner arm 318 is coaxially disposed with the longitudinal axis of mesh cage 20. When scoring discs 311 define the "DL", rotatable handle 316 is rotated relative to fixed body 313 to move scoring discs 311 towards each other until each scoring disc 311 engages mesh cage 20 as shown in FIG. 10. It will be appreciated that scoring discs 311 are aligned such that the cutting plane of each scoring disc 311 is aligned with the cutting plane of the other scoring disc 311. Rotatable handle 316 may be further rotated to apply a force to the portion of mesh cage 20 between scoring discs 311. The inner scoring disc 311 supporting mesh cage 20 to prevent crushing or deformation of mesh cage 20. When each scoring disc 311 engages mesh cage 20, scoring device 310 and mesh cage 20 are rotated relative to each other such that scoring discs 311 traverse the circumference of mesh cage 20. As scoring discs 311 traverse the circumference of mesh cage 20, scoring discs 311 rotate scoring the surface of mesh cage 20 creating a score mark 21. In embodiments, rotatable handle 316 can be rotated to apply additional force and/or reduce the gap between scoring discs 311 as mesh cage 20 and scoring device 310 are rotated. In some embodiments, scoring discs 311 cut through mesh cage 20 separating mesh cage 20 into a two portions 20a, 20b as shown in FIG. 11. In certain embodiments, a mandrel, e.g. mandrel 40 (FIG. 6A), is used to separate two portions 20a, 20b of mesh cage 20 as discussed above with respect to scoring device 10. In particular embodiments, mesh cage 20 can be positioned on a mandrel having a retainer mechanism 60, e.g. mandrel 50 (FIG. 7A), when mesh cage 20 is positioned about inner arm 318.

Figure 12:
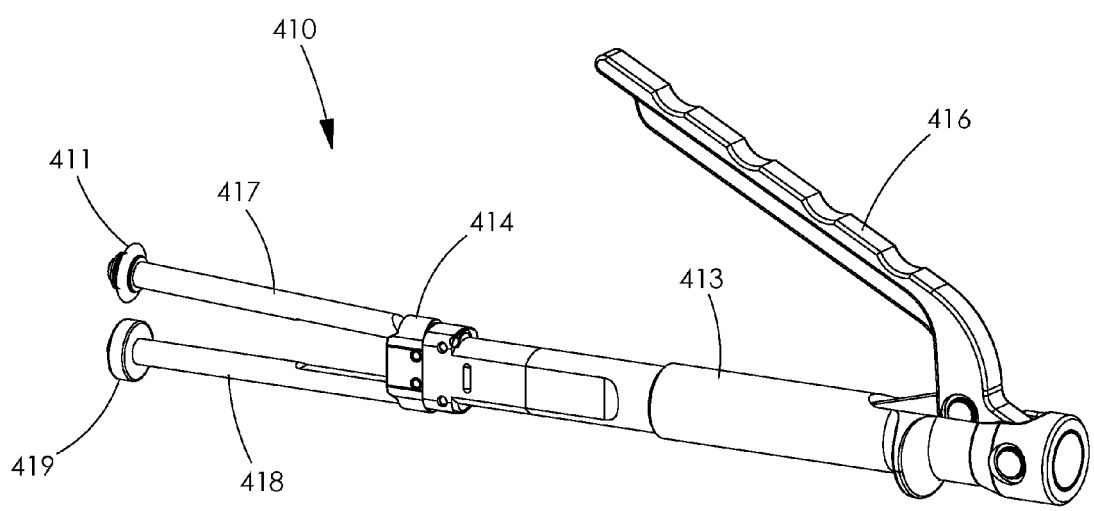
FIG. 12 is a perspective view of yet another scoring device in accordance with the present disclosure including a scoring disc and an anvil.

Referring to FIG. 12, still yet another scoring device 410 in accordance with the present disclosure incorporates a scoring disc 411, an anvil 419, a first or outer arm 417, a second or inner arm 418, and a fixed body 413. Scoring device 410 is substantially identical to scoring device 310, as such only the differences will be discussed.

Scoring disc 411 is positioned at the distal end of outer arm 417 and anvil 419 is positioned at the distal end of inner arm 418. It is also contemplated that scoring disc 411 can be positioned at the distal end of inner arm 418 and anvil 419 is positioned at the distal end of outer arm 417 Inner arm 418 is coupled to pivot joint 414 in a fixed position relative to fixed body 413 and outer arm 417 is movable relative to inner arm 418 as discussed above. It is also contemplated that outer arm 417 is coupled to pivot joint 414 in a fixed position relative to fixed body 413 and inner arm 418 is moveable relative to outer arm 417. A handle or lever 416 is operatively associated with outer arm 417 to move outer arm 417 relative to inner arm 418. As shown, when lever 416 is in an uncompressed position, scoring device 410 is in an open condition, similar to the open condition of scoring device 310, and when lever 416 is compressed towards fixed body 413 scoring device 410 is in a closed condition, similar to the closed condition of scoring device 310.

Scoring device 410 scores and/or cuts mesh cage 20 in a manner substantially similar to scoring device 310 with the anvil 419 supporting mesh cage 20 to prevent crushing or deformation of mesh cage 20.

Figure 13:
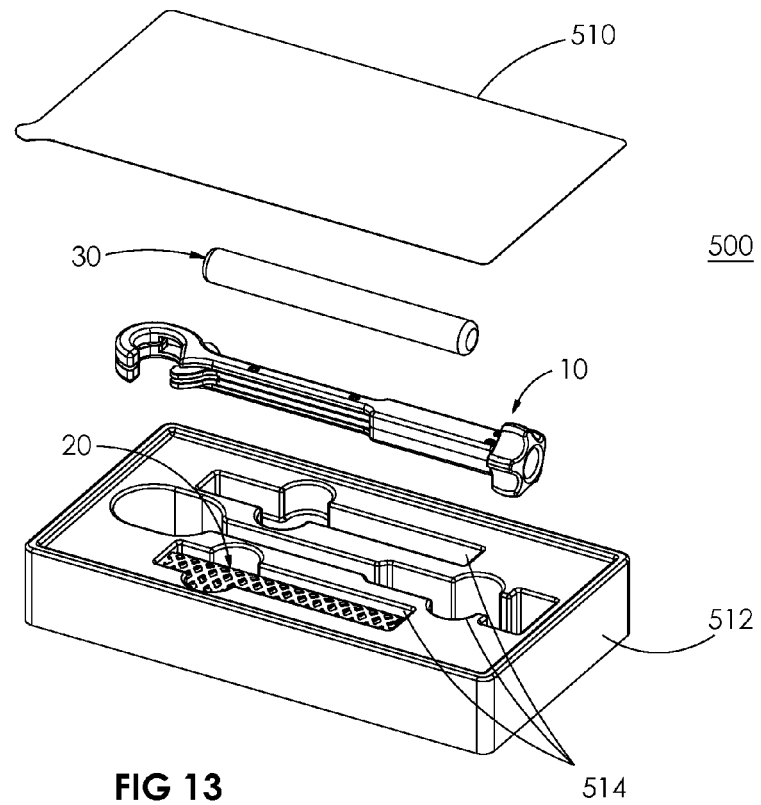
FIGS. 13 and 14 are perspective views of a kit in accordance with the present disclosure including a mesh cage and a scoring device.
Figure 14:
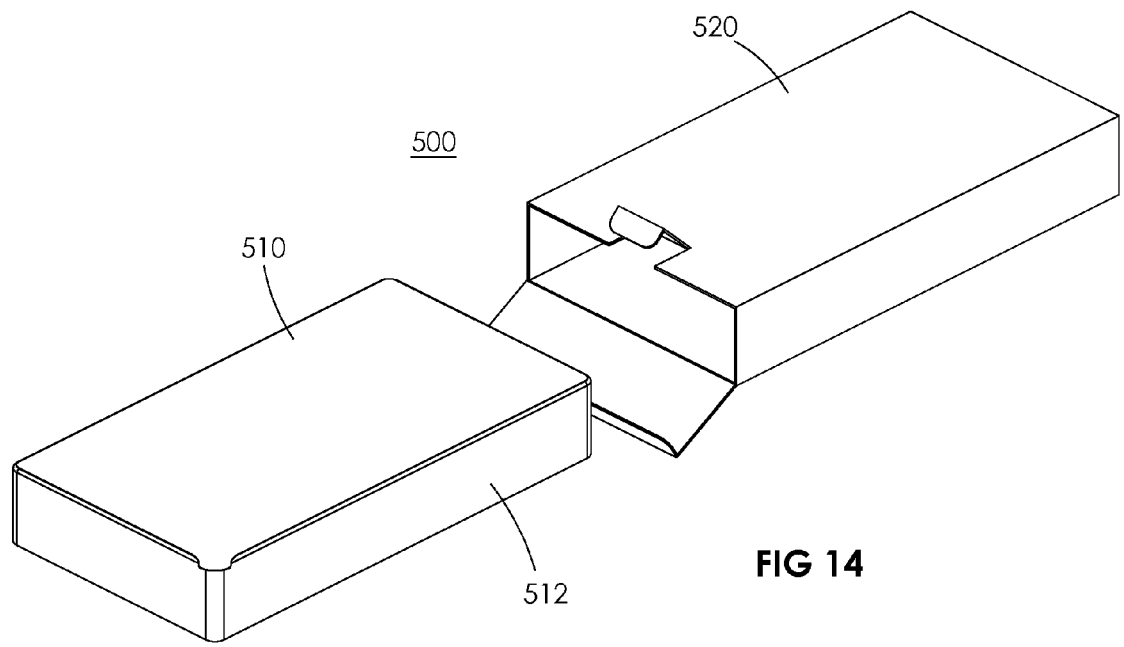

Referring to FIGS. 13 and 14, a kit 500 is provided in accordance with the present disclosure incorporating a scoring device 10, a mesh cage 20, and a mandrel 30 sealed within a sterile membrane 510. Kit 500 is shown with scoring device 10 and mandrel 30; however, kit 500 may alternatively include any of mandrels 30, 40, and 50 and scoring devices 10, 310, and 410. In embodiments, kit 500 includes two or more mandrels.

Kit 500 can include a sterile container 512 having cutouts 514 sized and configured to receive scoring device 10, mesh cage 20, and mandrel 30. Sterile membrane 510 is sized and configured to seal mesh cage 20, mandrel 20, and scoring device 310 within container 512 until needed by a clinician. Kit 500 can further include a box 520 that receives container 512.

In accordance with the present disclosure, a method for providing a mesh cage with a desired length includes providing a mesh cage with a length greater than the desired length, scoring the mesh cage at a desired length with a scoring device, and removing a length of the mesh cage beyond a score mark. It is contemplated that the method may incorporate any of the scoring devices 10, 310, and 410; mandrels 30, 40, and 50; and mesh cage 20.

Scoring the mesh cage may include creating a score mark at a desired length from an end of the mesh cage. Scoring the mesh cage may also include cutting the mesh cage. Scoring the mesh cage may further include rotating and/or oscillating the scoring device about the longitudinal axis of the mesh cage. In embodiments, scoring the mesh cage includes positioning the mesh cage about a mandrel. In some embodiments, scoring the mesh cage further includes inserting a pin through an opening in the mesh cage and a pin hole of the mandrel before scoring the mesh cage.

Removing a length of the mesh cage may include inserting a mandrel through an end of the mesh cage such that the end of the mandrel is positioned near the score mark and between the score mark and the end of the mesh cage which the mandrel is inserted and applying a force to the mandrel such that the mesh cage is cleanly separated into two portions at the score mark. In embodiments, a mandrel is inserted in each end of the mesh cage.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method for cutting a mesh cage including:
providing a mesh cage having first and second ends and having a first length;
positioning a scoring device about the mesh cage such that a distal end of a first arm of the scoring device is positioned adjacent an outer surface of the mesh cage and a distal end of a second arm of the scoring device is positioned within the mesh cage adjacent an inner surface of the mesh cage;
creating a score mark on the mesh cage at a position corresponding to a second length from an end of the mesh cage with the scoring device, the second length different from the first length; and
removing a portion of the mesh cage beyond the score mark.

2. The method of claim 1, wherein creating a score mark includes partially cutting through the mesh cage with the scoring device.

3. The method of claim 1, wherein creating a score mark includes rotating and/or oscillating the scoring device about a longitudinal axis of the mesh cage.

4. The method of claim 1, further including inserting a mandrel through an end of the mesh cage before creating a score mark, the mandrel including a cage support.

5. The method of claim 1, further including retaining the mesh cage in a fixed position to the cage support of the mandrel with a retaining mechanism.

6. A method for cutting a mesh cage including:
providing a mesh cage having first and second ends and having a first length;
creating a score mark on the mesh cage at a position corresponding to a second length from an end of the mesh cage with a scoring device, the second length different from the first length;
inserting an end of a first mandrel through the first end of the mesh cage and inserting an end of a second mandrel through the second end of the mesh cage after scoring the mesh cage, the end of the first mandrel positioned near the score mark between the score mark and the first end of the mesh cage and the end of the second mandrel positioned near the score mark between the score mark and the second end of the mesh cage; and
removing a portion of the mesh cage beyond the score mark.

7. The method of claim 6, further including applying a force to another end of each of the first mandrel and the second mandrel to remove the portion of the mesh cage beyond the score mark.

* * * * *